US011925568B2

(12) United States Patent
Elguizaoui

(10) Patent No.: US 11,925,568 B2
(45) Date of Patent: *Mar. 12, 2024

(54) CARTILAGE MEASUREMENT DEVICE AND METHOD OF USE

(71) Applicant: Sameh Elguizaoui, New York, NY (US)

(72) Inventor: Sameh Elguizaoui, New York, NY (US)

(73) Assignee: Sameh Elguizaoui, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/707,188

(22) Filed: Mar. 29, 2022

(65) Prior Publication Data

US 2022/0323239 A1   Oct. 13, 2022

Related U.S. Application Data

(63) Continuation of application No. 16/857,763, filed on Apr. 24, 2020, now Pat. No. 11,285,021.

(60) Provisional application No. 62/838,875, filed on Apr. 25, 2019.

(51) Int. Cl.
*A61F 2/46* (2006.01)
*A61F 2/30* (2006.01)

(52) U.S. Cl.
CPC ........ *A61F 2/4657* (2013.01); *A61F 2/30756* (2013.01); *A61F 2/4618* (2013.01); *A61F 2002/4662* (2013.01)

(58) Field of Classification Search
CPC ............ A61F 2/4657; A61F 2002/4662; A61F 2/4618; A61F 2/30756; A61B 2090/062
See application file for complete search history.

(56) References Cited

U.S. PATENT DOCUMENTS

| 5,312,216 A | 5/1994 | Hogg |
| 6,022,377 A | 2/2000 | Nuelle et al. |
| 2008/0065222 A1 | 3/2008 | Hamada |

OTHER PUBLICATIONS

Garrett, M.D., John C., "Allograft OATS® Resurfacing Technique for Articular Cartilage Restoration; Surgical Technique", Arthrex, Atlanta GA, 2016, pp. 1-8.

*Primary Examiner* — Javier G Blanco
(74) *Attorney, Agent, or Firm* — Lee Sullivan Shea & Smith LLP

(57) ABSTRACT

Disclosed herein is a device that helps to reduce the potential for inaccuracies and uncertainties associated with allograft cartilage transfer procedures. In one embodiment, the disclosed device generally includes a shaft, a stationary ring attached to the shaft, and a movable ring attached to the shaft and configured to move either toward the stationary ring or away from the stationary ring along the axis of the shaft. In practice, the device may be placed within a recipient cavity and adjusted such that one ring is positioned at the distal surface of the recipient cavity and the other ring is flush with the native cartilage surface of the recipient. The device may be removed from the recipient cavity, a donor graft placed within, and any excess donor graft extending beyond the rings trimmed off. The donor graft may then be removed from the device and inserted within the recipient cavity.

19 Claims, 6 Drawing Sheets

CARTILAGE MEASUREMENT DEVICE AND METHOD OF USE

CROSS-REFERENCE TO RELATED APPLICATIONS

This application is a continuation of and claims the benefit of priority under 35 U.S.C. § 120 to U.S. application Ser. No. 16/857,763, filed on Apr. 24, 2020 and titled "Cartilage Measurement Device and Method of Use," which claims the benefit of priority under 35 U.S.C. § 119(e) to U.S. Provisional Application No. 62/838,875, filed on Apr. 25, 2019 and titled "Cartilage Measurement Device and Method of Use," the contents of which are incorporated by reference herein in their entirety.

BACKGROUND

As a general matter, surgeons or other medical professionals have a swath of medical devices and other tools that they use to make medical procedures, such as surgeries, safe and efficient. To name a few, these tools include scalpels, reamers, measuring tapes, etc. Some tools, however, are rather rudimentary, which may result in any procedures that make use of such tools, prone to human error. As such, new and improved medical devices that result in a safer or more efficient procedure, or that generally reduce the chance for human error during the procedure, are advantageous and desired.

Overview

The present disclosure is directed to a medical device designed for use during allograft cartilage transfer procedures (and perhaps other types of medical procedures), and a method for engaging in an allograft cartilage transfer procedure or the like using such a device.

Current allograft cartilage transfer procedures (as well as perhaps other similar procedures) can involve rather rudimentary measuring and marking steps that may allow for human error during the procedure. For example, during a typical allograft cartilage transfer procedure, the surgeon will remove damaged cartilage from a recipient using a reaming device. After this removal, a cavity remains from which the damaged cartilage was removed. The surgeon typically measures the depth of this cavity using a measuring device. A measuring device is generally an elongated shaft, which can be flexible (like a measuring tape or flexible ruler) or rigid (like a probe), depending on the implementation. The measuring device generally has measurement markings displayed thereon, akin to a ruler or tape such that the surgeon can observe the measurement markings. To measure the depth of the cavity, the surgeon typically inserts the probe, ruler, or tape, as the case may be, into the cavity at multiple positions (e.g., at 12:00, 3:00, 6:00, and 9:00 positions, although other positions are possible), and at each position within the cavity the surgeon observes the depth of the cavity at that position as indicated by measurement markings on the measuring device. The surgeon then records these depths on paper or other recording medium.

Next, the surgeon obtains a graft from a donor, intending for this graft to be inserted into the recipient cavity created as described above. Typically, this graft is longer than necessary, so the surgeon will cut off any excess graft such that the graft fits flush within the recipient cavity. To do this, the surgeon recalls the recorded depths of the recipient cavity and marks these depths on the graft with a pen or other marking instrument. For instance, in the case that measurements were taken at 12:00, 3:00, 6:00, and 9:00 positions within the recipient cavity, the surgeon marks corresponding measurements on the distal end of the graft at corresponding 12:00, 3:00, 6:00, and 9:00 positions. The surgeon then connects these points by drawing a line with a pen or other marking instrument and trims off any portion of the distal end of the graft that extends beyond this line.

However, these steps are somewhat imprecise and prone to human error. For instance, the surgeon or an assistant may misread the measuring device and thus record an inaccurate measurement of the depth at one or more positions of the recipient cavity. Similarly, the surgeon or an assistant may inaccurately transfer the recorded measurements onto the graft. Even in cases where the surgeon accurately measures the depths of the recipient cavity and accurately transfers these measurements to the graft, the thickness of the pen marking, which indicates the measured depths, may contribute to uncertainty and result in an inaccurate trim of the distal end of the graft. Indeed, any one or more of these inaccuracies may result in a graft that does not appropriately fit within the recipient cavity, either because it is too long (as would be the case if not enough graft was trimmed off), too short (as would be the case if too much graft was trimmed off), or otherwise does not fit flush within the recipient cavity. These errors prolong the surgical procedure as steps may need to be repeated, and thus increase the cost and risks associated with the procedure.

To address one or more of these shortcomings, disclosed herein is a measuring device that helps to reduce the potential for inaccuracies and uncertainties associated with the measuring steps described above. The disclosed device generally includes (i) a shaft, (ii) a stationary ring attached to the shaft (where the stationary ring may have a few degrees of rotational freedom in any direction, as described in more detail below), and (iii) a movable ring attached to the shaft and configured to move either toward the stationary ring or away from the stationary ring along the axis of the shaft. Such a device may be used during allograft cartilage transfer procedures by, for instance, placing the device within the recipient cavity, adjusting the movable ring such that one ring is positioned at the distal surface of the recipient cavity and the other ring is flush with the native cartilage surface of the recipient. The movable ring may then be locked into place and the device may be removed from the recipient cavity. A donor graft may then be placed in the device, specifically within the stationary ring and the movable ring, and any distal portion of the donor graft that extends beyond the rings may be trimmed off while the graft is positioned within the device. The donor graft may then be removed from the device and inserted within the recipient cavity. Accordingly, using the device in this way may enable the surgeon to avoid having to separately measure multiple depths of the recipient cavity and transfer those measurements onto the graft itself, and thus may help reduce the risk of human error contributing to an inaccurate measurement and/or trim. Various embodiments and configurations of the disclosed device are described further herein.

Accordingly, in one aspect, disclosed herein is a device for use during a graft procedure, where the device comprises a shaft having a distal portion and a proximal portion, a proximal ring coupled to a proximal portion of the shaft, and a distal ring coupled to a distal portion of the shaft, wherein a given one of the proximal ring and the distal ring is movably coupled to the shaft and configured to move up and down along the axis of the shaft.

In another respect, disclosed herein a method for engaging in a graft procedure. In particular, the method may include positioning a device within a recipient cavity such that a distal ring of the device contacts a bottom surface of the cavity and a top surface of a proximal portion of the device is flush with a native surface surrounding the recipient cavity, actuating a locking mechanism that causes one of the proximal ring and the distal ring to be temporarily fixed in place in relation to the shaft, placing a donor graft within the device, and trimming an excess portion of the donor graft that extends beyond one of the proximal ring and the distal ring of the device.

One of ordinary skill in the art will appreciate these as well as numerous other aspects in reading the following disclosure.

DETAILED DESCRIPTION

As mentioned, disclosed herein is a measuring device that helps to reduce the potential for inaccuracies and uncertainties associated with the measuring steps described above. The disclosed device generally includes (i) a shaft, (ii) a stationary ring attached to the shaft, and (iii) a movable ring attached to the shaft and configured to move either toward the stationary ring or away from the stationary ring along the axis of the shaft. Such a device may be used during allograft cartilage transfer procedures by, for instance, placing the device within the recipient cavity, adjusting the movable ring such that one ring is positioned at the distal surface of the recipient cavity and the other ring is flush with the native cartilage surface of the recipient. The movable ring may then be locked into place and the device may be removed from the recipient cavity. A donor graft may then be placed in the device, specifically within the stationary ring and the movable ring, and any distal portion of the donor graft that extends beyond the rings may be trimmed off while the graft is positioned within the device. The donor graft may then be removed from the device and inserted within the recipient cavity. Accordingly, using the device in this way may enable the surgeon to avoid having to separately measure multiple depths of the recipient cavity and transfer those measurements onto the graft itself, and thus may help reduce the risk of human error contributing to an inaccurate measurement and/or trim. Various embodiments and configurations of the disclosed device will now be described.

Figure 2:
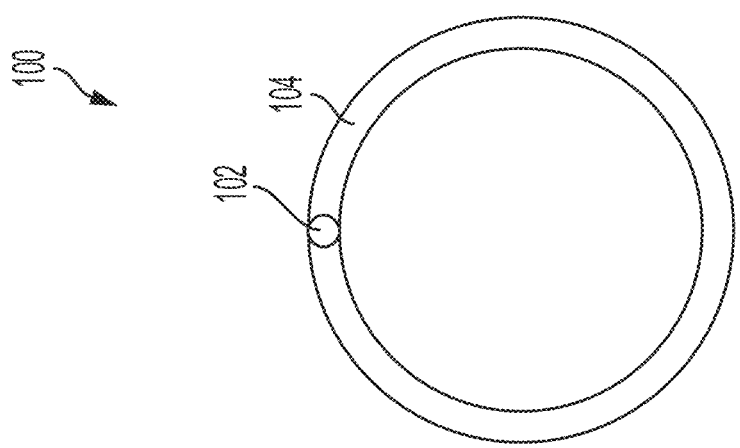
FIG. 2 is a top view of an example device in accordance with one example embodiment.
Figure 1:
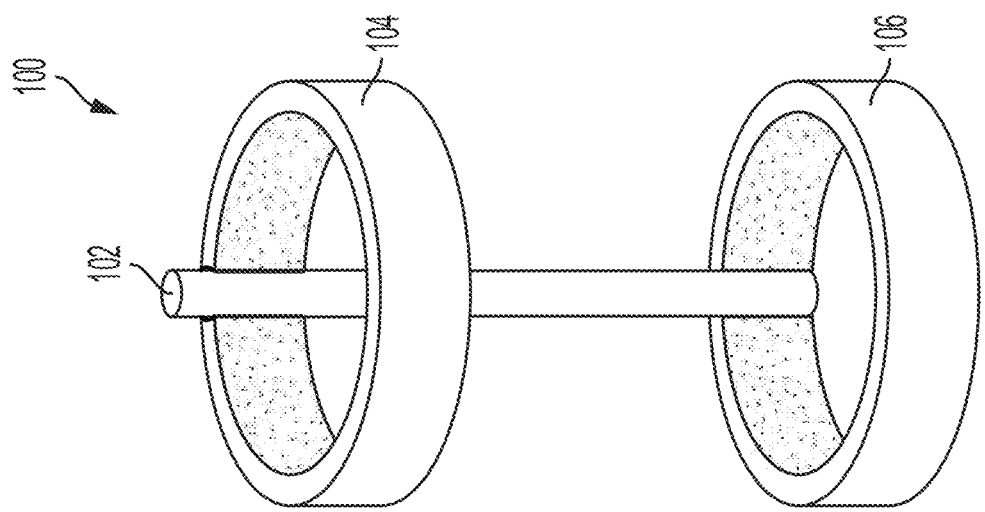
FIG. 1 is an isometric view of an example device in accordance with one example embodiment.

To help illustrate certain embodiments of the disclosed device, FIGS. 1-5 are provided. Turning first to FIGS. 1-2, FIG. 1 in particular is an isometric view depicting an example embodiment of the disclosed device 100, and FIG. 2 is a top-view depicting an example embodiment of the disclosed device 100. As depicted, the device 100 includes a shaft 102, a proximal ring 104, and a distal ring 106 (the proximal ring and/or the distal ring may at times herein be referred to as "element(s)"). The shaft 102 may generally be an elongated shaft, with a generally circular cross-section. Although shafts having differently-shaped cross-sections (e.g., rectangular, ovaloid, etc.) are possible as well.

In some embodiments, the proximal ring 104 and the distal ring 106 may take on a generally circular shape, however, in other embodiments, one or both of the proximal ring 104 and the distal ring 106 may take on a ovaloid or some other regular or irregular shape, or may be constructed of a generally pliable material that allows one or both of the proximal ring 104 and the distal ring 106 to take on any shape desired by the surgeon or other medical professional using the device 100. Further, the proximal ring 104 and/or the distal ring 106 may have any one of a number of differently shaped cross sections. As depicted throughout the figures, the rings are shown as having generally rectangular cross-sections. However, in other embodiments, the cross-sections of the proximal ring 104 and/or the distal ring 106 may be generally circular, ovaloid, or some other shape. And as a general matter, it should be understood that although the term "ring" is used to refer the proximal and distal elements (elements 104 and 106, respectively) of the device 100, within which a graft may be placed in accordance with the example embodiments disclosed further herein, these elements are not limited to being ring or circular shaped, and in other embodiments, these elements may take on ovaloid or any other regular or irregular shape.

Depending on whether the device 100 is embodied as a disposable device or a reusable device, the shaft 102, proximal ring 104, and distal ring 106 may be constructed of any suitable material or combination of materials, including, for example, titanium (if the device 100 is embodied as a reusable device), but other metals and other materials are possible, plastic (if the device 100 is embodied as a disposable device), or some combination of titanium (or other metal) and plastic (e.g., with the shaft 102 being titanium and perhaps reusable, and the proximal ring 104 and the distal ring 106 being plastic, and perhaps disposable). Further, in some embodiments, the proximal ring and/or the distal ring may be constructed of a generally pliable material, which may allow the rings to take on, or be formed during use, to the shape of the graft or cavity. Other materials and other combinations of materials are possible as well.

The proximal ring 104 and the distal ring 106 may be configured and attached to the shaft 102 in any number of different ways. As one possibility, the distal ring 106 may be fixed to a distal portion of the shaft 102 such that the bottom surface of the distal ring 106 is generally flush with the bottom surface of the shaft 102. The proximal ring 104 may be attached to a proximal portion of the shaft 102 but movable along the axis of shaft 102 either toward or away from the distal ring 106. To accommodate this, the shaft and/or the proximal ring 104 may include a locking mechanism, such as a clamp, which when actuated causes the proximal ring 104 to be temporarily or permanently fixed into place along the shaft 102.

As another possibility, the proximal ring 104 may be fixed to the shaft 102, whereas the distal ring 106 may be movable along the axis of the shaft 102 either toward or away from the proximal ring 104. To accomplish this, for instance, the distal ring 106 may be fixed to a distal portion of the shaft 102 but the distal portion of the shaft 102 may be configured to collapse within a proximal portion of the shaft 102, for instance, in a telescoping manner. In this configuration, the device 100 may also include a locking mechanism, such as a clasp, an internal spring configuration, or a variably-tapered shaft, such that when the distal ring 106 and the distal portion of the shaft 102 is moved to a desired location, the locking mechanism can be actuated (e.g., by engaging the clasp, or by rotating the shaft 360° to engage the spring or tapered portion of the shaft—although other locking mechanisms are possible) to cause the distal ring 106 and the distal portion of the shaft 102 to be temporarily or permanently fixed into place.

Alternatively, a proximal portion of the shaft 102 may be configured to collapse within a distal portion of the shaft 102. In this configuration, the device 100 may also include a locking mechanism (similar to that described above), such that when the proximal ring 104 and the proximal portion of the shaft 102 is moved to a desired location, the locking mechanism can be actuated (e.g., by engaging the clasp, or rotating the shaft 360° to engage the spring or tapered portion of the shaft—although other locking mechanisms are possible) to cause the proximal ring 104 and the proximal portion of the shaft 102 to be temporarily or permanently fixed into place.

As one additional example of a locking mechanism, the shaft 102 may include therein a movable wall portion that is pressed via a force (e.g., a spring force) outward toward the inner walls of the shaft in order to use friction to resist movement of the proximal portion of the shaft relative to the distal portion of the shaft. To control this, the shaft 102 may include at or near the proximal end thereof a handle with a button, such that when the button is depressed, the movable wall portion retracts so as to reduce or eliminate contact with the inner wall of the shaft 102. In this way, and so long as the button remains depressed, the proximal portion of the shaft 102 may freely slide up and down into the distal portion of the shaft 102. Once the proximal ring 104 and the distal ring 106 are at the desired positions, the button may be released, which may cause the movable wall portion to come back into contact with the inner walls of the shaft 102, which may thereby resist movement of the proximal portion of the shaft relative to the distal portion of the shaft. Still other mechanisms for moving and locking the rings into place along a shaft or other rigid body are possible as well.

Figure 3:
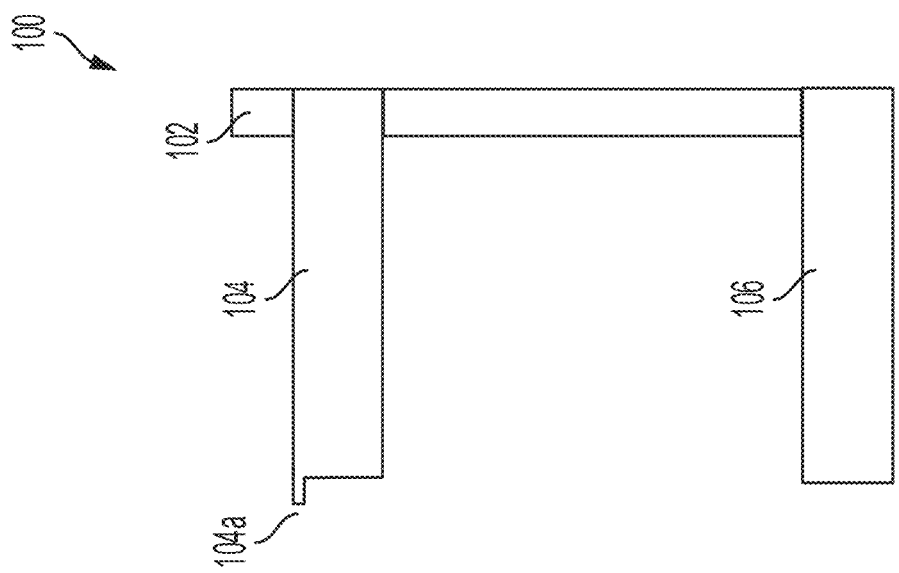
FIG. 3 is a side view of an example device in accordance with one example embodiment.

The device 100 may include additional features or be configured in alternative ways. To help illustrate one example additional feature, FIG. 3 is a side-view depicting an example embodiment of device 100. As depicted in this embodiment, proximal ring 104 may include a lip 104a that extends laterally from the proximal ring 104 and is constructed of a material (e.g., rubber or light-weight plastic) that allows for lip 104a bend into a position that is approximately perpendicular to the axis of the shaft 102. In practice, a lip on proximal ring 104, such as lip 104a, may assist in placement of the device 100 in a recipient cavity. For instance, in an allograft cartilage transfer procedure, placement of the device 100 in a recipient cavity such that lip 104a comes into contact with and rests upon the native cartilage surrounding the recipient cavity may help to ensure that the device 100 is in an appropriate alignment.

In an alternate embodiment, one or more of the proximal ring 104 or the distal ring 106 may be replaced with a plank. For instance, in one example, the proximal ring 104 may be replaced with a generally flat plank that may be movably attached to the shaft 102. In this way, when the device 100 is inserted into a recipient cavity such that the distal ring contacts the bottom surface of the cavity, the plank may be moved such that the plank rests flush against the native surface of the cartilage. Other embodiments in which the proximal ring 104 or the distal ring 106 take other forms may be possible as well.

Figure 4:
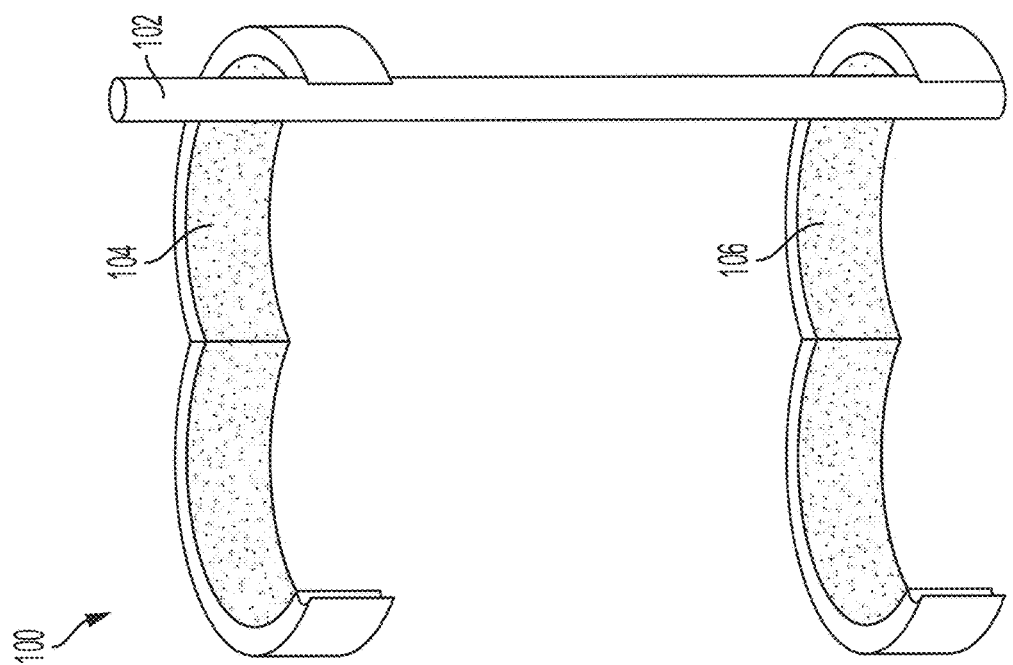
FIG. 4 is a side view of an example device in an example open position in accordance with one example embodiment.

Additionally, the proximal ring 104 and the distal ring 106 may be configured in various ways so as to allow the device 100 to receive the graft. As one possibility, device 100 may be configured with a hinge system such that the proximal ring 104 and the distal ring 106 can be "opened" to receive the graft. FIG. 4 is an isometric view depicting an example embodiment of device 100 that may be configured with a hinge system. As depicted in FIG. 4, the device 100 is in an "open" position, such that the proximal ring 104 and the distal ring 106 can receive a graft. Once the device 100 receives the graft, the device 100 may then be "closed" such that the proximal ring 104 and the distal ring 106 close around the graft to resume a shape resembling that of device 100 set forth in FIG. 1. In some embodiments, the device 100 has an additional clasp or other locking mechanism on one or more of the proximal ring 104 and/or the distal ring 106 in order to secure the rings around the graft.

Figure 5:
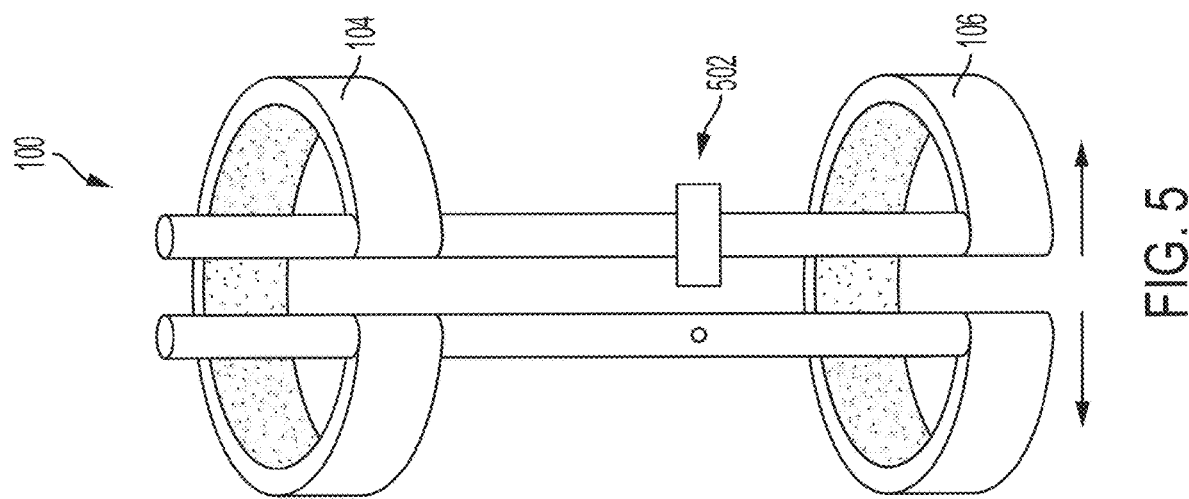
FIG. 5 is a rear view of an example device in accordance with one example embodiment.

As another possibility, device 100 may be configured to open at the shaft so as to receive the graft. For example, FIG. 5 depicts an example embodiment of device 100 that may be configured to open at the shaft 102. As depicted, the device 100 may bend apart slightly (in the direction of the depicted arrows) such that the shaft 102 splits into two separate portions. A graft can then be placed through this opening in the shaft 102. To accommodate this configuration, the proximal ring 104 and the distal ring 106 may be constructed of a somewhat flexible material in order for the rings to spread apart without permanently deforming. The device 100 may further include a clasping mechanism 502 in order to close the device 100 and temporarily prevent the device 100 from opening inadvertently. In other configurations, the proximal ring 104 and the distal ring 106 may be configured with a hinge system as described above in connection with FIG. 4 to further facilitate opening and closing the device 100 at the shaft.

It will be appreciated that the devices depicted in FIGS. 4-5 are example embodiments of devices that are configured with a hinge system and/or to spread apart at the shaft, and in other embodiments, hinges or other mechanism for facilitating "opening" of the rings may be placed in other locations and may be configured in other manners.

In some embodiments, the device 100 may include a wire mesh that surrounds the device 100. In particular, the wire mesh may be attached to the device 100 at the proximal ring 104 and extend downward and attach to the distal ring 106 thus forming a generally cylindrical mesh attached to the device 100 at the proximal and distal rings. In such embodiments, as the proximal ring 104 or the distal ring 106 is moved along the axis of the shaft 102, the wire mesh may accordingly expand or contract. In some configurations, the device 100 may include the wire mesh but may not include one or more of the distal ring 104 and/or the proximal ring 106. In such configurations, the wire mesh may be attached to the shaft 102 and configured to expand or contract in order to match the depth and contour of the recipient cavity. Other configurations are possible as well.

In some embodiments, the proximal ring 104 and the distal ring 106 may have fixed diameters. In such cases, the device 100 can be referred to as having a "size," where the "size" is the diameter of the rings. In practice, multiple devices 100 of different sizes may be available to a surgeon at the outset of a given procedure. Then, depending on the size of the cavity created by the reaming device during the procedure, the surgeon would select a given device 100 that has a size that matches the size of the cavity created by the reaming device.

In some embodiments, the device 100 may be configured with a proximal ring 104 and a distal ring 106 that have adjustable diameters. This can be accomplished in many different ways. As one possibility, the rings may be configured such that the material that comprises the ring folds around on itself and is fed through a clasp. Excess material can be fed through the clasp to increase the diameter, and excess material can be pulled through the clasp to decrease the diameter. Once the desired diameter of the ring is achieved, by, for instance, pulling an amount of material through the clasp to decrease the diameter or by feeding an amount of material through the clasp to increase the diameter, the clasp can be locked and the remaining excess material can be trimmed off. Measurement indicators may be printed on the excess material at various positions such that if the clasp were to be locked at any given position of the material, the ring diameter would match the diameter indicated by the measurement indicator located at that particular position. Other example configurations in which the proximal ring 104 and a distal ring 106 that have adjustable diameters are possible as well.

In some embodiments, the proximal ring 104 and/or the distal ring 106 may be configured to have several degrees of rotational freedom. In particular, the proximal ring 104 and/or the distal ring 106 may be configured to attach to the shaft using a mechanism (e.g., a ball-and-socket—although other mechanisms are possible) that enables the respective ring to attach to the shaft 102 yet pivot in place and thus rotate a few degrees in any of a number of directions. This may help facilitate a more accurate graft measurement in scenarios in which the distal surface of the recipient cavity may be at an incline with respect to the axis of shaft 102 of the device 100. Accordingly, when device 100 having, for instance, a rotationally-free distal ring 106 is inserted into a recipient cavity having an inclined (or otherwise uneven or unlevel) distal surface, the distal ring 106 can pivot slightly and accommodate this surface. When the distal ring 106 is locked into place, the locking mechanism may serve also to lock into place the rotational position of the distal ring 106 (e.g., by clamping down on a ball-and-socket joint mechanism and thereby using friction to resist additional rotation—although other locking mechanisms are possible). As such, the device 100 may help provide for a more accurate measurement, cut, and positioning of the graft into the recipient cavity, particularly when the distal surface of the recipient cavity is inclined or otherwise uneven or unlevel. Other configurations providing for a rotatable proximal ring 104 and/or a rotatable distal ring 106 are possible as well.

Figure 6:
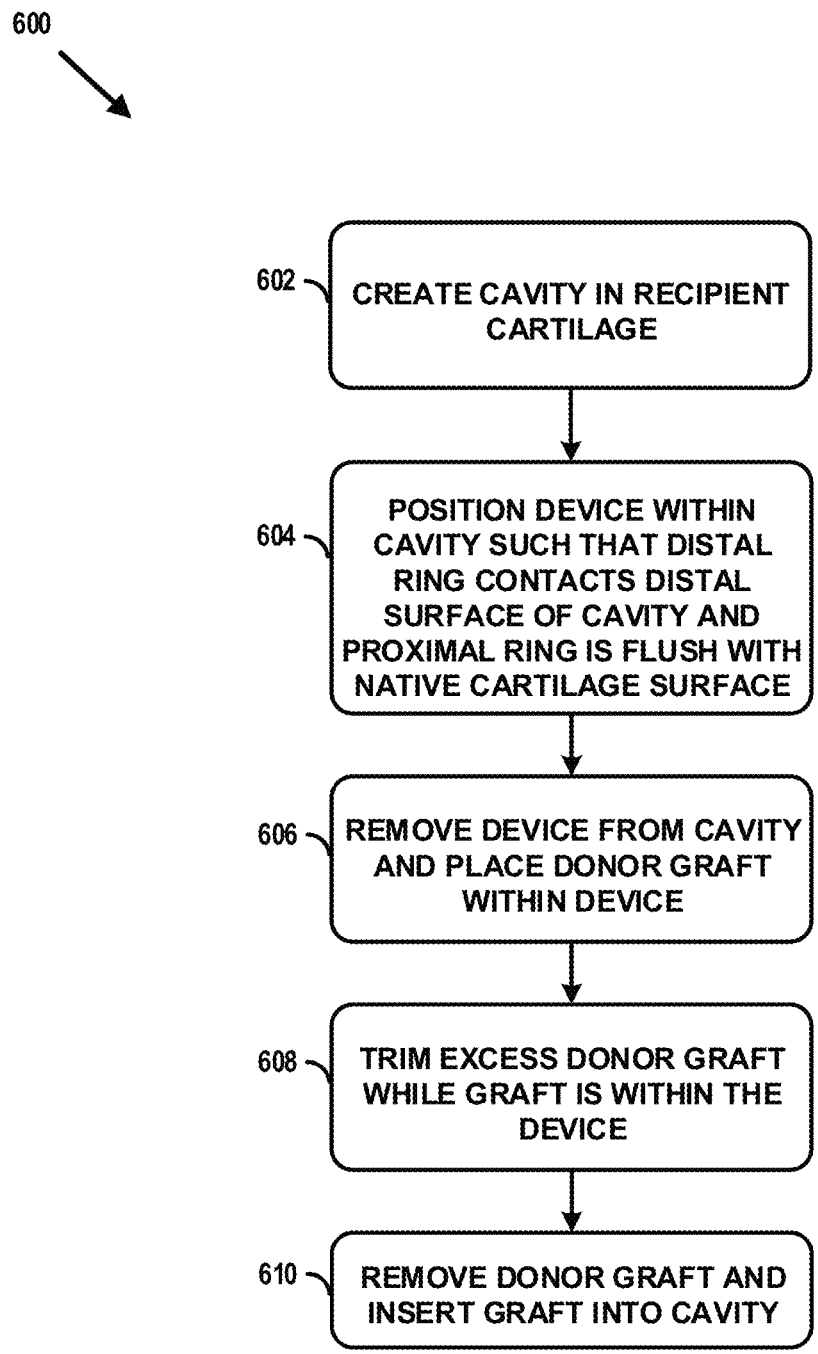
FIG. 6. depicts a flow diagram showing some example steps that may be included in a procedure utilizing an example embodiment of the disclosed device.

To help describe an example of how the disclosed device may be used during an allograft cartilage transfer procedure, reference is now made to FIG. 6, which depicts an example block diagram 600. For the purposes of illustration, block diagram 600 illustrates example steps that may be used in the course of conducting an allograft cartilage transfer procedure using the disclosed device. However, it should be understood that the block diagram 600 depicted in FIG. 6 is merely described in such manner for the sake of clarity and explanation and that some steps may be carried out in various other manners as well, including the possibility that example steps may be added, removed, rearranged into different orders, grouped together, and/or not grouped together at all.

Figure 7:
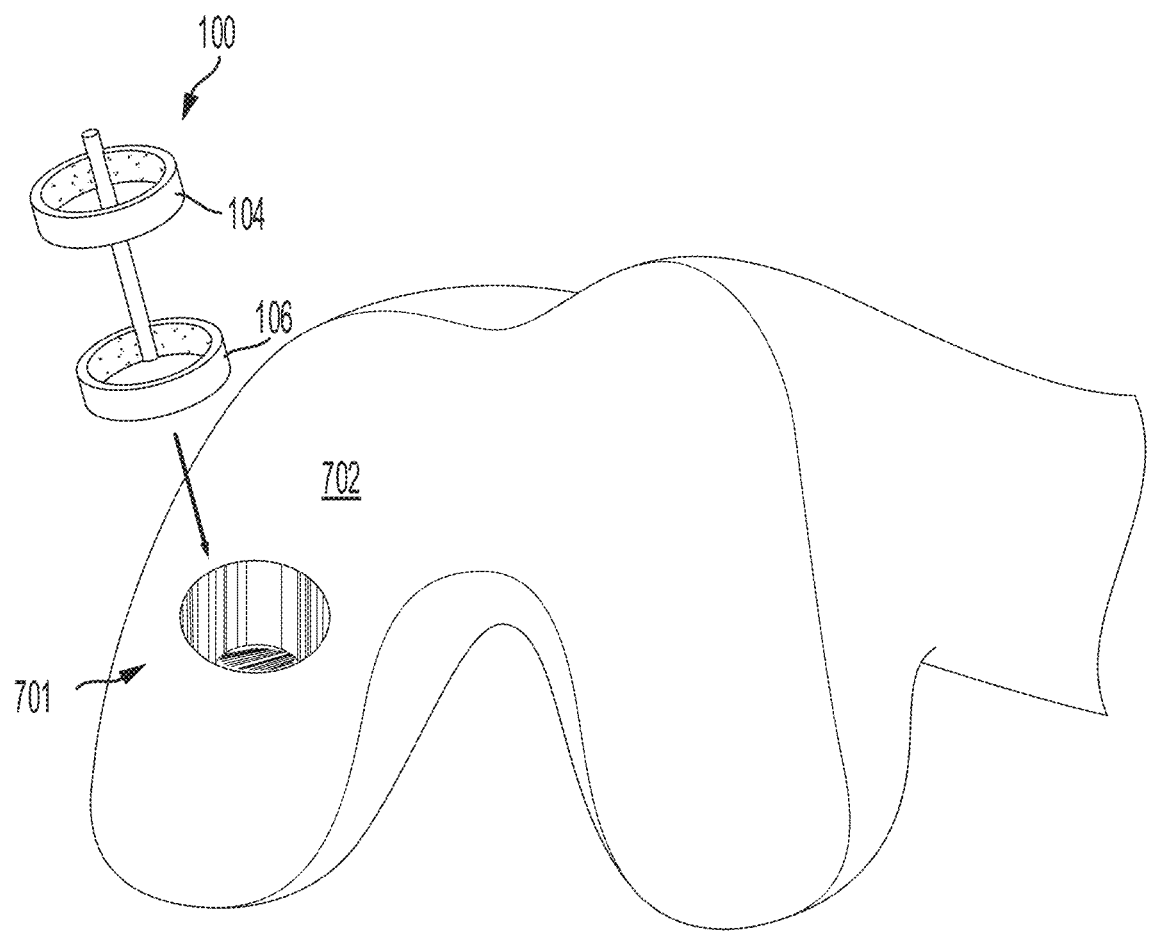
FIG. 7 depicts an example cavity in recipient cartilage with which an example embodiment of the disclosed device may be used.

Turning first to block 602, a surgeon or other medical professional may create a cavity in the recipient cartilage. As mentioned above, the surgeon or other medical professional may identify a defect in a recipient's cartilage and subsequently use a reamer or other device to remove the defect, which thus leaves a cavity in the cartilage and perhaps in a portion of any bone underlying the cartilage. To illustrate one example of this, FIG. 7 depicts an example portion of cartilage that includes a cavity 701, which may be created by a surgeon or other medical professional using a reamer or other similar device. Other ways to create a cavity in recipient cartilage may be possible as well.

Figure 8:
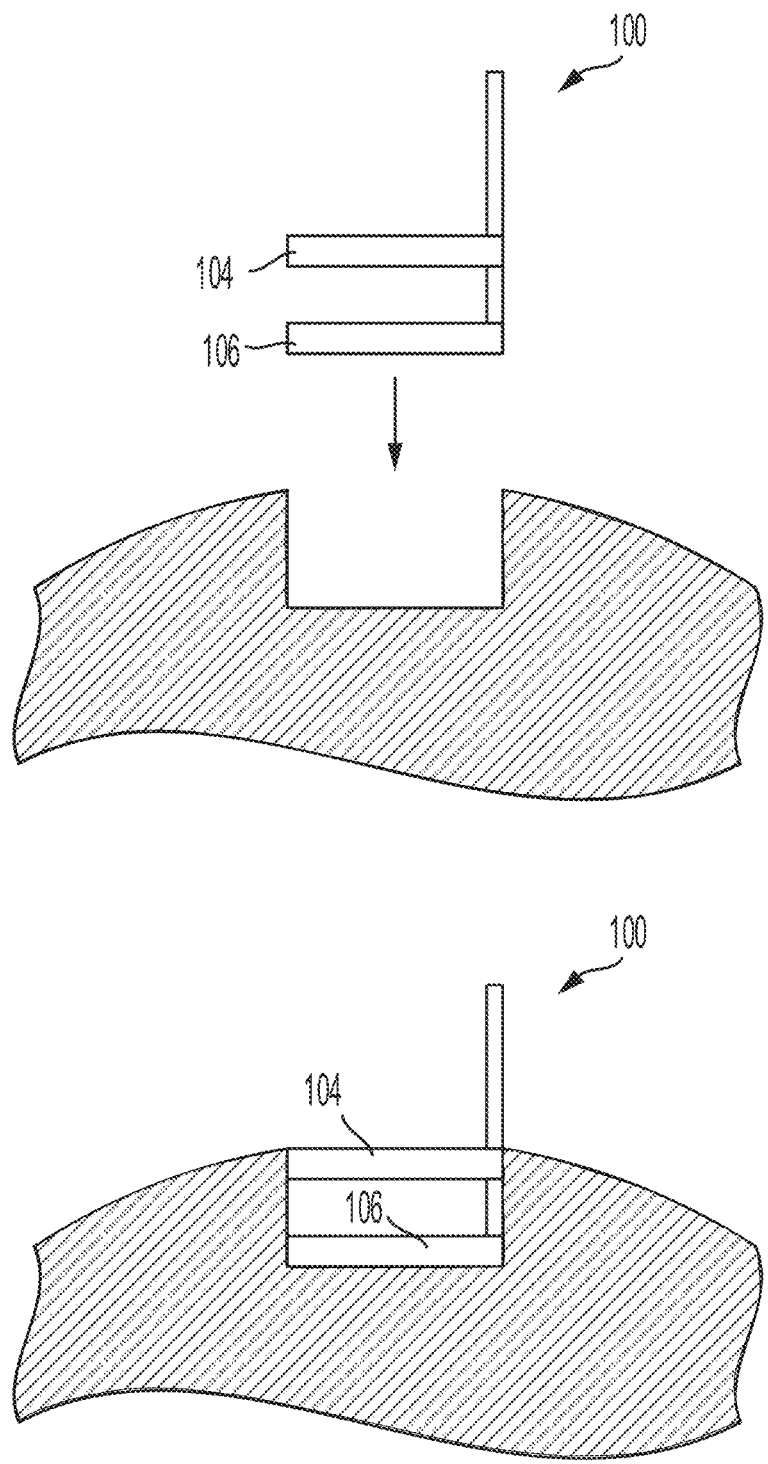
FIG. 8 depicts an example cross-section of a cavity in recipient cartilage with which an example embodiment of the disclosed device may be used.

Next at block 604, the surgeon or other medical professional may position the disclosed device within the cavity such that the distal ring of the device contacts or sits against the distal surface of the cavity and the proximal ring is flush with the native cartilage surface. In one example usage, the surgeon or other medical professional may insert device 100 in the cavity 701 until the distal ring 106 sits against the bottom surface of the cavity. The surgeon or other medical professional may then reposition the rings of the device until the proximal ring sits flush with the native surface of the recipient cartilage. To help illustrate one example of this, FIG. 8 depicts a cross section of the example portion of cartilage depicted in FIG. 7. As depicted, device 100 may be positioned within the cavity created in the recipient cartilage. The device may then be adjusted such that the distal ring 106 sits against the bottom surface of the cavity and the proximal ring 104 sits flush with the native cartilage surface, as depicted.

Depending on the embodiment of the device 100, adjusting of the device such that the distal ring 106 sits against the bottom surface of the cavity and the proximal ring 104 sits flush with the native cartilage surface can take place in a number of different ways. For instance, in embodiments in which the proximal ring 104 is movable along the axis of the shaft 102, the surgeon or other medical professional may position the proximal ring 104 along the axis of the shaft 102 so that the proximal ring 104 sits flush with the native surface of the cartilage 702. In embodiments in which the distal ring 106 is movable along the axis of the shaft 102, the surgeon or other medical professional may position the distal ring 106 along the axis of the shaft 102 so that the proximal ring 104 sits flush with the native surface of the cartilage 702 and the distal ring 106 sits against the bottom surface of the cavity. As an alternative to positioning the device 100 such that the proximal ring 104 sits flush with the native surface 702 of the cartilage, the surgeon or other medical professional may position the device in any manner that would allow a donor graft to be placed within the device, trimmed, and then placed within the recipient cavity such that the top surface of the donor graft sits flush with the native surface of the recipient cartilage.

Once the surgeon or other medical professional has positioned the disclosed device within the cavity such that the distal ring of the device contacts or sits against the distal surface of the cavity and the proximal ring is flush with the native cartilage surface, the surgeon or other medical professional may actuate a locking mechanism (e.g., which may be one or more of the types of locking mechanisms discussed above) in order to lock the positions of the proximal and distal rings. In one example of this, and depending on the embodiment of locking mechanism used, the surgeon or other medical professional may actuate the locking mechanism while the device is positioned within the cavity. As an another example, the surgeon or other medical professional may hold the position of the proximal and distal rings steady, remove the device from the recipient cavity, and then actuate the locking mechanism once the device has been removed from the recipient cavity. Other ways to actuate the locking mechanism on the device may be possible as well.

Figure 9:
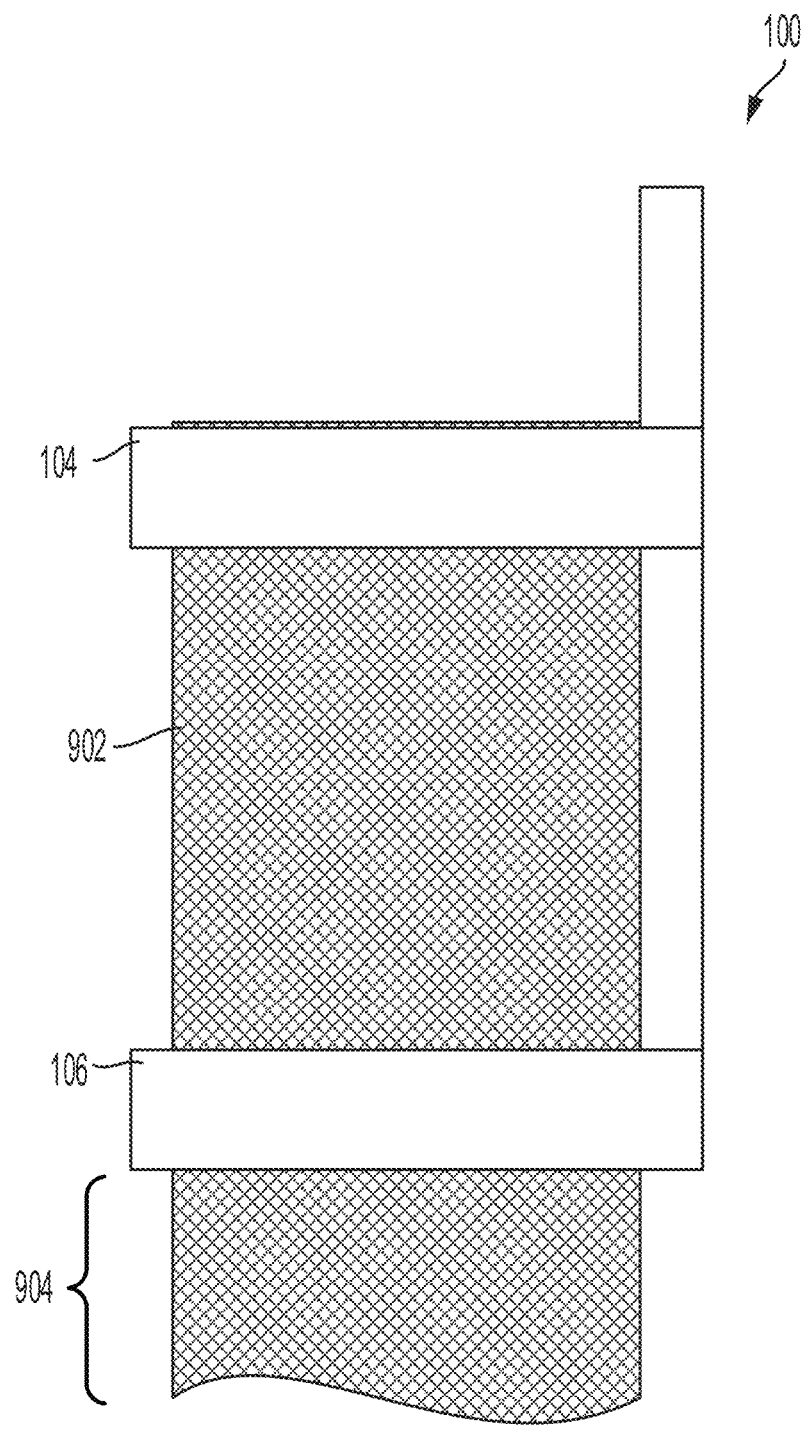
FIG. 9 depicts an example embodiment of the disclosed device that contains an example portion of a donor graft.

Turning back to block diagram 600 in FIG. 6, next at block 606, the surgeon or other medical professional may remove the device from the cavity and, with the positions of the rings locked in place, place a donor graft within the device. As explained, the surgeon or other medical professional may do this by sliding a donor graft through the rings or opening the rings or otherwise spreading the rings apart such that a donor graft can be placed inside the rings, depending on the embodiment of the device. To help illustrate one example of a donor graft placed within the device 100, FIG. 9 depicts one example of a device 100 and a donor graft 902 positioned within the device 100. As depicted, the donor graft may be positioned within the device such that the top surface of the donor graft sits as close as possible to being flush with the top (or proximal) surface of the proximal ring 104. Once the donor graft is positioned within the device 100 and the top surface of the graft sits flush with the proximal surface of the proximal ring 104, the surgeon or other medical professional may determine whether the donor graft is sufficiently long in order to continue the procedure with that graft. For instance, if the graft does not visibly protrude from the bottom (or distal) surface of the distal ring 106, then the graft may not be long enough to use in the recipient cavity. If the graft visibility protrudes from the distal surface of the distal ring 106, then the graft length may be determined to be sufficient, and the surgeon or other medical professional may proceed to trim the graft down to size at block 608. As depicted in FIG. 9, for instance, graft 902 has a portion 904 that visibly protrudes from the distal surface of distal ring 906.

Next at block 608, the surgeon or other medical professional may, while the graft is within the device, trim any excess portions of the donor graft that extends beyond the distal ring of the device. The surgeon or other medical professional may use any appropriate cutting instrument for this step, such as a saw or any other cutting instrument.

Next at block 610, the surgeon or other medical professional may remove the donor graft from the device and insert the donor graft into the recipient cavity. From here, the surgeon or other medical professional may proceed with any remaining portions of the allograft cartilage transfer procedure and may complete the procedure.

Example embodiments of the disclosed innovations have been described above. Those skilled in the art will understand, however, that changes and modifications may be made to the embodiments described without departing from the true scope and sprit of the present invention, which will be defined by claims.

For instance, those in the art will understand that the disclosed device may be implemented in other medical or surgical contexts. The disclosed approaches for using the disclosed device could be used in other contexts as well.

Further, to the extent that examples described herein involve operations performed or initiated by actors, such as "humans," "operators," "users" or other entities, this is for purposes of example and explanation only. Claims should not be construed as requiring action by such actors unless explicitly recited in claim language.

The invention claimed is:

1. A cartilage measurement device for use during a graft procedure, the cartilage measurement device comprising:
   a shaft having (i) a proximal portion and (ii) a distal portion that is configured to collapse at least partially within the proximal portion and expand out of the proximal portion;
   a distal ring coupled to the distal portion of the shaft;
   a proximal ring coupled to the proximal portion of the shaft; and
   a locking mechanism, that, when actuated, is configured to cause the distal portion of the shaft to be temporarily fixed in place within the proximal portion of the shaft, the locking mechanism comprising at least one of a clasp, an internal spring configuration, a tapered internal portion of the shaft, or a movable wall portion of the shaft,
   wherein the cartilage measurement device is sized and configured to be positioned within a cavity formed in a native cartilage of a patient,
   wherein the proximal and distal rings are coaxial and are configured to receive a graft therethrough, and
   wherein the cartilage measurement device is further configured such that when the cartilage measurement device is positioned within the cavity, the distal ring contacts a bottom surface of the cavity.

2. The cartilage measurement device of claim 1, wherein the cartilage measurement device is further configured such that when the cartilage measurement device is positioned within the cavity, a top surface of the proximal ring is aligned with a top surface of the native cartilage.

3. The cartilage measurement device of claim 1, wherein the shaft is formed from a reusable material that comprises a metal material.

4. The cartilage measurement device of claim 1, wherein the shaft is formed from a disposable material that comprises a plastic material.

5. The cartilage measurement device of claim 1, wherein one or both of the distal ring or the proximal ring are formed from a pliable material that is configured to be adapted to a respective form of one or both of the cavity or the graft.

6. The cartilage measurement device of claim 1, wherein each of the proximal ring and the distal ring comprises an outer cartilage-contacting surface and an inner graft-contacting surface.

7. The cartilage measurement device of claim 1, further comprising a hinge system whereby at least one of the proximal ring or the distal ring can be positioned in an open position so as to receive the graft.

8. The cartilage measurement device of claim 1, wherein the shaft comprises a first shaft portion and a second shaft portion, and wherein the cartilage measurement device is configured to receive the graft between the first shaft portion and the second shaft portion.

9. The cartilage measurement device of claim 1, wherein at least one of the proximal ring or the distal ring is configured to have an adjustable diameter.

10. The cartilage measurement device of claim 1, wherein at least one of the proximal ring or the distal ring is coupled to the shaft such that the at least one of the proximal ring or the distal ring has rotational freedom relative to the shaft and is configured to be pivoted in place while coupled to the shaft.

11. The cartilage measurement device of claim 10, wherein the locking mechanism, when actuated, is further configured to cause the proximal ring to be temporarily fixed in place such that the proximal ring no longer has rotational freedom and is no longer configured to be pivoted.

12. A method comprising:
providing a cartilage measurement device for use during a graft procedure, the cartilage measurement device comprising:
a shaft having (i) a proximal portion and (ii) a distal portion that is configured to collapse at least partially within the proximal portion and expand out of the proximal portion;
a distal ring coupled to the distal portion of the shaft;
a proximal ring coupled to the proximal portion of the shaft; and
a locking mechanism, that, when actuated, is configured to cause the distal portion of the shaft to be temporarily fixed in place within the proximal portion of the shaft, the locking mechanism comprising at least one of a clasp, an internal spring configuration, a tapered internal portion of the shaft, or a movable wall portion of the shaft,
positioning the cartilage measurement device within a cavity formed in a native cartilage of a patient, and
placing a graft through the proximal and distal rings, wherein the proximal and distal rings are coaxial,
wherein when the cartilage measurement device is positioned within the cavity, the distal ring contacts a bottom surface of the cavity.

13. The method of claim 12, wherein positioning the cartilage measurement device within the cavity comprises:
positioning the cartilage measurement device within the cavity such that a top surface of the proximal ring is aligned with a top surface of the native cartilage.

14. The method of claim 12, wherein the shaft is formed from a reusable material that comprises a metal material.

15. The method of claim 12, wherein the shaft is formed from a disposable material that comprises a plastic material.

16. The method of claim 12, wherein one or both of the distal ring or the proximal ring are formed from a pliable material that is configured to be adapted to a respective form of one or both of the cavity or the graft.

17. The method of claim 12, wherein each of the proximal ring and the distal ring comprises an outer cartilage-contacting surface and an inner graft-contacting surface.

18. The method of claim 12, wherein the cartilage measurement device further comprises a hinge system, the method further comprising:
positioning at least one of the proximal ring or the distal ring in an open position for receiving the graft.

19. The method of claim 12, wherein the shaft comprises a first shaft portion and a second shaft portion, the method further comprising:
placing the cartilage measurement device between the first shaft portion and the second shaft portion.

* * * * *